(12) United States Patent
Uckelmann et al.

(10) Patent No.: US 8,524,142 B2
(45) Date of Patent: Sep. 3, 2013

(54) APPARATUS AND PROCESS FOR CONTINUOUS GENERATIVE PRODUCTION

(75) Inventors: Ingo Uckelmann, Bremen (DE); Andreas Schwartz, Schwanenwede (DE)

(73) Assignee: BEGO Medical GmbH, Bremen (DE)

( * ) Notice: Subject to any disclaimer, the term of this patent is extended or adjusted under 35 U.S.C. 154(b) by 57 days.

(21) Appl. No.: 12/861,295

(22) Filed: Aug. 23, 2010

(65) Prior Publication Data

US 2011/0049739 A1 Mar. 3, 2011

(30) Foreign Application Priority Data

Aug. 25, 2009 (EP) .................................... 09168560

(51) Int. Cl.
*A61C 13/00* (2006.01)

(52) U.S. Cl.
USPC ............ 264/497; 264/16; 264/17; 264/297.1; 264/482

(58) Field of Classification Search
USPC ...................... 264/16, 17, 19, 297.1, 482, 497
See application file for complete search history.

(56) References Cited

U.S. PATENT DOCUMENTS

| | | | |
|---|---|---|---|
| 4,759,887 A * | 7/1988 | Geissler et al. ................ 264/414 |
| 4,863,538 A * | 9/1989 | Deckard ........................ 264/497 |
| 5,753,274 A | 5/1998 | Wilkening et al. |
| 6,106,747 A * | 8/2000 | Wohlwend ...................... 264/16 |
| 6,217,816 B1 * | 4/2001 | Tang .............................. 264/497 |
| 6,554,600 B1 * | 4/2003 | Hofmann et al. ........... 425/174.4 |
| 6,939,489 B2 * | 9/2005 | Moszner et al. ................ 264/16 |
| 7,189,344 B2 * | 3/2007 | Rheinberger et al. ........... 264/16 |
| 8,287,794 B2 * | 10/2012 | Pax et al. ........................ 264/308 |
| 2002/0167100 A1 * | 11/2002 | Moszner et al. ................ 264/16 |
| 2003/0003180 A1 * | 1/2003 | Farnworth et al. ......... 425/174.4 |
| 2003/0003380 A1 * | 1/2003 | Farnworth et al. .............. 430/18 |
| 2003/0074096 A1 * | 4/2003 | Das et al. ...................... 700/119 |
| 2003/0155667 A1 * | 8/2003 | Devoe et al. .................. 264/1.27 |
| 2003/0205849 A1 * | 11/2003 | Farnworth .................... 264/401 |
| 2004/0031780 A1 * | 2/2004 | Hagemeister et al. ... 219/121.85 |
| 2005/0186538 A1 * | 8/2005 | Uckelmann ................ 433/201.1 |
| 2006/0003095 A1 * | 1/2006 | Bullen et al. .................. 427/180 |
| 2006/0186101 A1 * | 8/2006 | Hagemeister et al. ... 219/121.85 |

(Continued)

FOREIGN PATENT DOCUMENTS

| | | | |
|---|---|---|---|
| CA | 2 295 896 A1 | 7/2000 |
| EP | 0 734 842 A1 | 10/1996 |

(Continued)

*Primary Examiner* — Christina Johnson
*Assistant Examiner* — Saeed Huda
(74) *Attorney, Agent, or Firm* — Kilpatrick Townsend and Stockton LLP

(57) ABSTRACT

The invention concerns a process for producing products of individual geometry, in particular dental prostheses or dental auxiliary parts, comprising the steps of producing a plurality of products on the surface of a substrate plate by means of selective hardening, in particular by means of selective sintering or melting, in which the material is applied in successive layers, after each layer application one or more predetermined regions of the applied layer is selectively hardened by means of an energy-rich radiation and connected to one or more regions of the subjacent layer, wherein the predetermined regions are predetermined on the basis of a cross-sectional geometry of the product in the respective layer. According to the invention the successive layers are applied in layer planes oriented inclinedly relative to the surface of the substrate plate. The invention further concerns an apparatus for carrying out such a process.

10 Claims, 4 Drawing Sheets

(56) References Cited

U.S. PATENT DOCUMENTS

Figure 1:
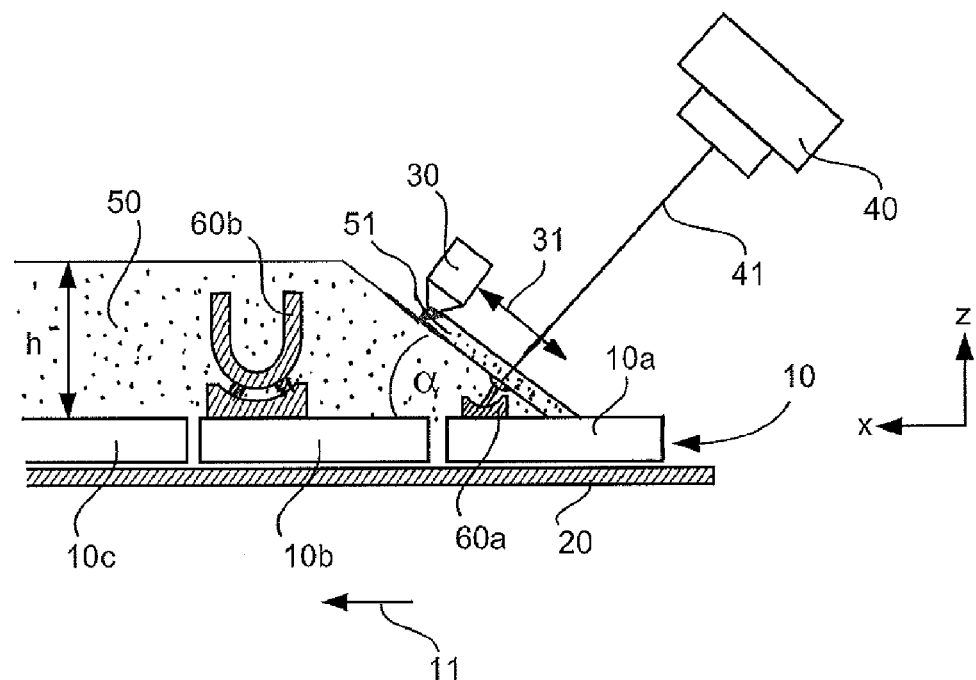

| | | | |
|---|---|---|---|
| 2007/0173967 A1* | 7/2007 | Kritchman et al. | 700/119 |
| 2007/0235904 A1* | 10/2007 | Saikin | 264/497 |
| 2008/0085828 A1* | 4/2008 | Khan et al. | 501/152 |
| 2008/0131104 A1* | 6/2008 | Philippi | 392/407 |
| 2008/0241392 A1* | 10/2008 | Dimter et al. | 427/256 |
| 2009/0045553 A1* | 2/2009 | Weidinger et al. | 264/497 |
| 2009/0189315 A1* | 7/2009 | Gunster et al. | 264/442 |
| 2011/0180971 A1* | 7/2011 | Vagt et al. | 264/401 |
| 2011/0190904 A1* | 8/2011 | Lechmann et al. | 623/23.61 |
| 2011/0316178 A1* | 12/2011 | Uckelmann | 264/16 |

FOREIGN PATENT DOCUMENTS

| | | |
|---|---|---|
| EP | 1 021 997 B1 | 5/2007 |
| WO | WO 2004/014636 A1 | 2/2004 |
| WO | WO 2008/128502 A2 | 10/2008 |

\* cited by examiner

APPARATUS AND PROCESS FOR CONTINUOUS GENERATIVE PRODUCTION

This application claims benefit of priority of European Application No. 09 168 560.2, filed Aug. 25, 2009, the disclosure of which is herein incorporated by reference.

The invention concerns a process for producing products of individual geometry, in particular dental prostheses or dental auxiliary parts, comprising the steps of producing a plurality of products on the surface of a substrate plate by means of selective hardening, in particular by means of selective sintering or melting, in which the material is applied in successive layers, after each layer application one or more predetermined regions of the applied layer is selectively hardened by means of an energy-rich radiation and joined to one or more regions of the subjacent layer, wherein the predetermined regions are predetermined on the basis of the cross-sectional geometry of the product in the respective layer. A further aspect of the invention is an apparatus for carrying out such a process.

Generative production processes, that is to say production processes in which a material is shaped to give an individual product in an additive production procedure are used in the area of the production of prototypes and in the meantime have also been brought into use in product production, in particular in the manufacture of individually shaped products or small-scale series. EP 1 021 997 B1 discloses for example producing individually shaped dental prostheses or dental auxiliary parts by means of a selective laser sintering process involving given parameters.

Besides such a laser sintering or laser melting process (SLS, SLM) which is particularly suitable for dental prostheses, for metallic powders, other generative production process can also be suitable for other products, for example processes in which a granular material or another solid material is sintered or melted by a high-energy beam such as for example a laser beam or an electron beam and in that way joined and hardened, or processes in which a plastic material in solid or liquid form is selectively hardened by a high-energy beam such as for example a laser or focused light beam by photopolymerisation.

Those generative production processes usually operate in such a way that layers of the hardenable material are successively applied to a substrate plate, for example by the substrate plate being successively and discontinuously lowered into a liquid bath of the hardenable material or by successive layers being applied to the substrate plate in mutually superposed relationship by means of a powder application apparatus. After each layer application operation certain parts of the layer are selectively hardened and the product is built-up layer-wise in that way. After the product is finished by hardening of the last layer, non-hardened regions of the material can be removed and can be frequently re-used. The SLS or SLM process is described in principle in EP 0 734 842 A1, the disclosure of which in that respect is entirely incorporated herein.

A fundamental problem with generative production processes is the long period of time which elapses between generating the production data and finishing the product. It is known for a plurality of products to be simultaneously generatively built up on a substrate plate in order in that way to increase the number of products produced in a given period of time. That procedure is appropriate in particular when dealing with products of very small dimensions in relation to the dimensions of the substrate plate and leads to an effective increase in productivity.

It is known from EP 0 734 842 A1 for the stoppage time of a production apparatus to be reduced by a procedure whereby a substrate plate which is releasably fixed on a carrier is used and in that way, immediately after the products are finished on that substrate plate, the substrate plate can be removed and replaced by a fresh substrate plate to start a new manufacturing procedure. While that configuration makes it possible for the time required to remove the products from the substrate plate not to be part of the stoppage time of the production apparatus, the apparatus still suffers from the disadvantage that it is only when the production data of all products which are to be produced on a substrate plate are available, that the production procedure can be started and as a result the total time for the production of a product, in particular in the case of individual production of many small products, cannot be decisively reduced.

WO 2008/128502 discloses an apparatus which follows the same basic concept and provides a conveyor device within the production apparatus, with which one or more building containers and metering or supply containers can be conveyed in order thereby to achieve simple, fast reliable powder handling within the production apparatus. By using that apparatus, production of products in a building container by means of a powder material can be quickly implemented and subsequently, after those products are finished, production of products using a different powder material can be effected in a second building container. It will be noted however that, with this production apparatus, the production procedure also requires at least as much time as elapses between generation of the production data for all products on the substrate plate and finishing of the products, so that production in relation to each individual one of a multiplicity of products which are formed still requires a comparatively long period of time.

WO 2004/014636 discloses a process for layer-wise generative production of three-dimensional objects, in which a plurality of objects are simultaneously produced in two building regions. In that case, a layer is applied in one building region and selective hardening is effected in another building region by means of radiation. Four process chambers are provided, which can be in the form of spatially mutually separated individual chambers or in the form of subregions having two double chambers or a quadruple chamber. It is further provided that a laser can be connected to a respective one of the process chambers by way of a switching-over arrangement. The described apparatus and the process described for generative production of products with that apparatus suffer from the disadvantage that, for the purposes of simultaneous production with alternate hardening and layer application in the respective process chambers, separate control of the application operation in each of the process chambers is required. The apparatus and the process are admittedly suitable for the complicated and expensive special application involved in the production of a plurality of products with different starting materials in correspondingly different process chambers, but the production procedure and the apparatus is complicated and expensive both in terms of structure and also in terms of control and can therefore be further optimised in regard to its productivity in efficiency for the production of numerous small products and the time which elapses between final generation of the production data for a product and finishing of the product itself.

While the known production processes and apparatuses can only be used to produce individual products whose size approximately occupies the substrate plate, both in a productive mode of operation and also with an overall production time which is viable for each individual product, for products whose dimensions are much smaller than the substrate plate, it is only possible to ensure productivity by the joint production of a plurality of products on a substrate plate, but the production time for an individual product in that case cannot be a desirably short period of time, but is increased by the generation of production data for all products to be produced on the substrate plate, and the subsequent simultaneous production of all products.

A further problem in generative production of small products, which expression is intended to denote products whose base area is smaller than the surface of the substrate plate, in particular being smaller by at least one order of magnitude, is that, in many areas of use involving individual product geometries, generative production is effected in the form of individual-order production, such as for example in the production of dental prostheses in dental laboratories. In that case the individual orders typically do not arrive at the same time at the user of the production apparatus, but in time-displaced relationship. In order to achieve high productivity and utilisation of the installation in that case, the user must combine a plurality of orders together, in order to produce the products contained in the combined orders on a substrate plate at the same time. However, in particular for the order which has been first received, that involves a considerable delay between receipt of the order and finishing the product. If in contrast the user wishes to service each order in the shortest possible time and to produce the corresponding individual product, he is obliged to carry out the production process on a substrate plate with only one or a few products, and that leads to a generally low level of utilisation of the production apparatus and low productivity.

An object of the invention is to further develop the known production processes in such a way that both high productivity and also a short production time for each individual product is achieved when dealing with products, the dimensions of which are small in comparison with the size of the substrate plate. A further aim of the invention is to provide a production process and a production apparatus which curtail the period of time between the receipt of an order for a small product which is to be produced individually, and the time of finishing the product, without in that case detrimentally influencing the productivity of the production process or the production apparatus.

According to the invention those objects are attained by a process of the kind set forth in the opening part of this specification, in which the successive layers are applied in layer planes oriented inclinedly relative to the surface of the substrate plate.

The process according to the invention also provides that a plurality of products are produced simultaneously on the surface of a substrate plate by a selective hardening operation in layer-wise fashion. In that respect it will be understood that, with the process according to the invention, a substrate plate of classic design does not necessarily have to be used, that is to say a round or square or rectangular one-piece substrate plate. Instead, the substrate plate according to the invention can be provided for example in the form of a substrate conveyor belt or in the form of a substrate plate which is composed of a plurality of segments and in which those substrate plate segments are arranged in a row for example in one direction.

The process according to the invention is distinguished in that the layers of the hardenable material are not applied in such a way that the layer plane is oriented parallel to the surface of the substrate plate, but instead they are applied in such a way that the layer plane is oriented inclinedly, that is to say at an angle of between 0 and 90°, relative to the surface of the substrate plate. That inclined layer application on the substrate plate provides that the material bed thickness arranged in total therefore at a location on the substrate plate is not the same at every location, but differs. In particular the thickness of the applied material bed increases starting from a region in which there is precisely one layer thickness on the substrate plate, continuously to a region in which the maximum applied layers can be placed above the substrate plate. It is to be appreciated in that respect that a material layer is always applied over a region of the substrate plate which admittedly does not necessarily have to extend over the entire substrate plate, but generally extends over a region in which a plurality of products which are built up on the substrate are arranged.

The inclined application of the material layers in accordance with the invention means that a plurality of small products are built up simultaneously on the substrate plate with the process according to the invention, but those products are at different stages in their production. Thus, in a region in which only a single layer is present on the substrate plate due to the inclined application of the layer, a new product can be begun, whereas a product can be finished in a region in which the inclinedly applied layer is applied to a plurality of already previously applied layers. Between those two end points, there can be one or more products at a stage in production which is between the beginning and the end, that is to say with for example 50 or 100 layers which have already been applied and selectively hardened.

As a result, the production process according to the invention makes it possible to begin with the production of a product immediately after the generation of the production data for the product has been finished and then to remove that product from the production process after it has been finished, without in that case having to wait until production data for other products have been finished or indeed other products themselves have been finished. It will be appreciated in that respect that, in the same way as quasi-continuous commencement of production of successive individual products is implemented with the process according to the invention, quasi-continuous removal of individual finished products can be effected in order to minimise the production time for each individual product. It is thus possible with the process according to the invention also to produce products of small dimensions in such a production time which is only required by virtue of the production steps necessary for the individual layer applications and hardening thereof, and nonetheless to achieve a high level of productivity by virtue of the parallel production of a plurality of products, insofar as the inclined application of powder in relation to the substrate plate makes it possible to produce products at different stages in production on a substrate plate and with a common layer application. The application of powder is preferably effected along a seal which is in opposite relationship to the direction of flow of the powder in the layer, caused by the force of gravity, when the layer extends inclinedly relative to the horizontal.

In a first preferred embodiment it is provided that the successive layers are applied in mutually parallel relationship. Parallel application of the layers permits a uniform layer thickness along the entire application procedure and a process control system which is thus simple. It will be appreciated in that respect that each of the layers does not necessarily have to be of the same thickness, in particular the layer thickness can be larger or smaller in dependence on the product geometry in order to adapt the geometrical resolution which is predetermined by the layer thickness, to the product geometry.

In accordance with a further preferred embodiment it is provided that each of the successive layers is applied at an angle which is smaller than or equal to the angle of repose of the material on the substrate plate. Basically in that respect the angle at which a layer is applied is to be interpreted as the angle which is included as an acute angle between the plane of the surface of the substrate plate and the plane of the applied layer. The term angle of repose of the material is used to denote that angle which occurs between the side surfaces of a pile of material and a base surface to which the material is applied by way of heaping it up. The angle of repose of a material is correspondingly smaller, the greater the slidability of the material on the surface to which it is applied, and the greater the slidability of the material in itself, that is to say for example the slidability of the individual grains of powder of a powder material relative to each other. If the successive layers in the process according to the invention are applied at an angle which is less than the angle of repose or corresponds to the angle of repose, it is possible in that way to ensure that an applied layer does not subsequently lose its applied geometrical shape by virtue of pieces of the layer or individual particles of material or the like slipping down. Instead, in regard to selecting such an angle of application, this ensures that the layer remains stable as a free sloping embankment and consequently can be selectively hardened in a simple and geometrically precise fashion.

To positively influence the angle of repose, that is to say, to achieve an angle of repose which is as large as possible and consequently also to be able to apply the layers at the largest possible angle, on the one hand the surface of the substrate can be processed in a specific fashion, for example by polishing, grinding, lapping, honing, etching, rotofinishing, sandblasting, milling, turning and other machining processes. In that case the production process can preferably be of such a nature that a substrate plate roughness which is advantageous for a large angle of repose is achieved, which is typically in the range of 0.5 μm to 50 μm Rz (averaged roughness depth in accordance with DIN EN ISO 4287:1998) or typically in the range of 0.1 μm to 10 μm Ra (mean roughness value) or is in the range of 0.04 mm to 1.3 mm RSm (mean groove width in accordance with DIN EN ISO 4287:1998 in relation to periodic profiles as is to be found for example in relation to milling). It is to be appreciated in that respect that these preferred roughness ranges for the substrate plate are advantageous for typical powders used for selective laser sintering or selective laser melting, in particular thereby to produce small parts such as dental implants or auxiliary parts which are true to shape and precise.

Preferably moreover the surface of the powder can be processed by means of polishing, grinding, etching, sandblasting, rotofinishing or coating to positively influence the angle of repose in the above-indicated fashion.

If liquid materials are used as the hardenable material, wettability of the surface can be positively influenced by a chemical, optical or mechanical surface treatment, such as for example laser beam roughening.

A further starting point for positively influencing the angle of repose in the above-indicated sense is the above-mentioned granulation of the material. That can be effected for example by pouring molten metal in a thin jet into cold water with steady agitation to obtain a granulated material in that way. Other easily meltable metals can be granulated by pouring them into a container which is heavily covered with chalk on the inside wall and shaking it after the container has been closed until the metal has cooled down.

In that respect it is particularly advantageous for the process and apparatus according to the invention if the material is processed in such a way as to achieve a good connection, clamping effect or the like in respect of the material particles with each other and to achieve correspondingly poor slidability of the particles against each other, in other words, the particles should be in particular of an external configuration differing from a spherical shape and at the same time should have high surface roughness and in particular should preferably further be of an overall irregular configuration. Slidability of the material influences at the same time the suitability thereof for being applied in thin layers and assuming dense packing with small proportions of cavities in the layer. The material must therefore be processed in such a way that on the one hand a maximum angle of repose is achieved. On the other hand it must be possible to apply the material in the layer thicknesses which are suited to the process, and it is necessary to achieve a packing density which is as high as possible as that is directly related to the density achieved for the product produced. Typical layer thicknesses are between 5 μm and 200 μm.

In a further preferred embodiment it is provided that the substrate plate is displaced between two successive layer application operations with a directional component perpendicularly to the plane in which the layer is applied. In this context the expression directional component is used to denote a component of movement which jointly with other components of movement which take place in other directions, makes up the overall movement. By virtue of a component of movement perpendicularly to the plane of the layer application, it is possible to produce an advance which permits a subsequent layer application, without the layer application apparatus having to be moved in any other way than parallel to the plane of the layer application, for that purpose. In particular, that directional component can be implemented by the substrate plate being moved in a direction parallel to the surface of the substrate plate. By virtue of the angle between that surface and the plane of the layer application, such a movement includes the directional component required for the advance movement necessary in the successive layer application operation.

It is further particularly preferred if the surface of the substrate plate in the region in which the layers are applied extends horizontally in relation to the direction of the force of gravity. In that case the layer is applied in a plane which extends inclinedly relative to the horizontal and the layer application apparatus has to be designed for such a layer application inclinedly relative to the horizontal.

In a preferred embodiment which is an alternative thereto it is provided that the surface of the substrate, in the region in which the layers are applied, extends inclinedly relative to the horizontal in relation to the direction of the force of gravity. Because the surface of the substrate plate extends inclinedly relative to the horizontal in the layer application region, that makes it possible for the layer to be applied in a horizontal plane. The layer application apparatus can accordingly be designed for a movement in a horizontal plane. In that respect it is to be appreciated that, even when the substrate plate extends inclinedly relative to the horizontal, it is possible to implement the application of material which also extends inclinedly relative to the horizontal and the material application apparatus can be designed accordingly.

In the two aforementioned embodiments it is further preferably provided that the applied layers are displaced into an adjacent production portion in the form of a holding region which is disposed adjacent to a production portion in which the layers are applied, and in which an upper surface, formed by the applied layers, of the applied material, is covered and supported by a lower surface of a cover plate, the lower surface extending parallel to the surface of the substrate plate. In that configuration, in a given production portion in which the height of the material above the substrate plate has reached a given height, support for the material is effected by on the one hand the support plate and on the other hand a cover plate. In that case the spacing between the substrate plate and the cover plate corresponds to the maximum height of the layer bed, that is to say the number of layers multiplied by the layer thickness. The provision of such a cover plate means that the material can be favourably stabilised on the substrate plate and as a result the inclined layer application can be implemented in geometrically precise and reproducible fashion. In that case the cover plate comes into contact with the respective end regions of the material layers, that face away from the support plate, and support them. It is to be appreciated in that respect that the cover plate can also be in the form of an endless conveyor belt or a plate which also moves along therewith and which moves synchronously with the movement of the substrate plate. That avoids a relative movement between the applied material and the cover plate which otherwise could result in disturbing the regularity of the layer application in the edge region in relation to the cover plate.

In a further preferred embodiment the surface of the substrate plate is subdivided into a first surface of a first substrate plate segment and at least one further surface of a further substrate plate segment. In this development the substrate plate is subdivided into two or more adjacent substrate plate segments. In that respect the term substrate plate segment is used to denote a portion of the substrate plate, that is separate in terms of production technology, and which can be defined solely on the basis of control data of the layer application and the hardening sequence. In that case a substrate plate segment represents the region of the substrate plate, on which there are produced one or more products which can be removed at the same time from the substrate plate, because they are begun and finished virtually at the same time.

The term substrate plate segment can however also mean in particular a physically separate component. In that case the substrate plate is composed of a plurality of segments which are joined together. In that case the segments can also be used to build up one or more products on a respective segment, which products can be begun and finished at the same time and can then be detached from the substrate plate segment.

In that respect it is particularly preferred if the substrate plate segments are connected releasably to each other or releasably to a main or base carrier and each substrate plate segment, after the production of one or more products on its surface, is detached from an adjacent substrate plate segment or the main carrier in order to feed the product or products thereon to further processing steps. That development makes it possible for each substrate plate segment to be removed from the production apparatus in order to feed the finished products disposed thereon to further processing steps. Such further processing steps can be for example careful separation of the product from the substrate plate segment, a subsequent cutting machining operation, subsequent hardening and the like.

In that respect it is still further particularly preferred if the substrate plate segments are so provided in mutually juxtaposed relationship in the production portion in which the layers are applied, that no material can pass through between the substrate plate segments. The provision of the substrate plate segments in such a fashion is particularly advantageous if layers are applied over a plurality of substrate plate segments in one working operation, with a single layer application apparatus. In that case, material from a layer application is prevented from being able to pass through between the substrate plate segments, which could result on the one hand in undesirable loss of material and on the other side geometrical influencing of the layer thickness and the layer configuration. That can be achieved for example if the substrate plate segments bear directly against each other with mutually congruent edge portions or if a suitable separate seal is disposed between two substrate plate segments.

It is still further preferred if the substrate plate segments are in the form of segments of an endless conveyor apparatus. The substrate plate segments can be for example fixed to an endless conveyor belt or can be connected together in such a way that they form such an endless conveyor belt, in the form of a link-type chain. In that case the substrate plate segments can be moved in successive relationship along an upper run and a lower run, wherein layer application and selective layer hardening are effected during the movement along the upper run. The removal of unhardened applied material from the intermediate space between the produced products and removal of the products can also be effected in the region of the upper run, for example by suitable suction removal devices or mechanical separation apparatuses. It is however also possible in the same fashion for the removal of unhardened material to be implemented in the region of the lower run or at the transition from the upper run to the lower run, for example under the effect of the force of gravity, and the finished products can then either be removed together with a substrate plate segment or directly from the substrate plate segment in the region of the lower run.

In a further preferred embodiment it is provided that the substrate plate segments are of such a configuration and arrangement that a first product or a group of first products is built up on a single substrate plate segment and a further product or a group of further products is built up on a further one or a plurality of further substrate plate segments. With this configuration on the one hand one or more products can be produced on a single substrate plate segment in order in that way to produce small products in a very fast production time with a high level of productivity. On the other hand it is also possible to produce a single product on a plurality of substrate plate segments. That can be advantageous in particular when larger products are to be produced with the process according to the invention, that is to say those products whose longitudinal extent or contact surface is larger than the surface of a substrate plate segment. It is still further provided that a group of a plurality of products can be produced on two or more substrate plate segments. That can be required in particular in relation to products which extend very far in only one given direction. Thus the process according to the invention makes it possible to manufacture a product whose length extends over a plurality of substrate bed segments. If a plurality of such products are to be produced, then in accordance with this development a group of such products can be formed and that group can then be produced extending over a plurality of substrate plate segments.

The process according to the invention is distinguished in particular in that the material is applied as a coherent layer to the first and the at least one further substrate plate segment and selectively hardened, in such a way that the maximum spacing between the first substrate plate segment and a layer portion of the layer, which is applied thereto to produce the first product, in at least one and preferably a plurality of and in particular all stages in the process, differs from the maximum spacing between the further substrate plate segment and a layer portion of the layer, that is applied thereto for production of the further product. In accordance with the process according to the invention therefore the material is present at least in one stage of the production process, in such a fashion that the spacing between a first substrate plate region and the layer applied over that region is greater than the spacing between another substrate plate region and the layer which is applied over that other region and which is the same layer as previously. The process according to the invention can be still further developed by the steps of: removing material which is arranged on the first substrate plate segment and which has not hardened, without in that case removing material of a further substrate plate segment, and subsequently removing material which is arranged on a further substrate plate segment and which has not hardened. For the quasi-continuous generative production according to the invention, it is particularly advantageous at the removal location if removal of the unhardened material can be effected in such a way that an adjacent region is not influenced thereby and the unhardened material remains in place in that adjacent region. During generative production the unhardened material has a support function and serves to receive and carry layers disposed thereover. Therefore in general the unhardened material may not be removed before the product has not been completely built up and hardened. In order now under such a precondition to avoid the necessity that finished products must firstly cover a longer distance serving for process assurance until they reach the removal location at which the unhardened material is removed, it is advantageous if the material removal apparatus can implement the material removal operation without in that case affecting the directly adjacent region. That permits fast and quasi-continuous production and avoids providing a safety margin spacing between the layer application apparatus and the material removal apparatus.

It is still further preferred that in a first phase of the production operation only layer regions of a layer which serve to produce the first product are selectively hardened and in a last phase of the production operation only layer regions of a layer are selectively hardened, which serve to produce the further product and preferably in a middle phase of the production operation, that is between the first and last phases, layer regions of a layer which serve to produce the first and the further product are hardened. Quasi-continuous and simultaneous production of products which is achieved in that way in different production stages provides a productive and rapid process for the individual production of small products by means of a generative production process.

It is still further preferred if provided between the substrate plate segments is a separating wall which separates the building space above each substrate plate segment from the building space above an adjacent substrate plate segment. Such a separating wall permits or simplifies the removal of unhardened material above a substrate plate segment without in that case affecting the unhardened material in a substrate plate segment adjacent thereto. In that respect it is to be appreciated that such a separating wall can be provided as a component part of the production apparatus and in that case for example can be of such a design configuration that it is trackingly guided simultaneously with the layer application operation in order in each case to be of the exact height or somewhat less than the exact height of the application of material in the region between two substrate plate segments.

In accordance with an embodiment which is preferred in this respect it is provided that the separating wall is produced by hardening of the applied material during the operation of producing the product or products. With this development such a separating wall is respectively produced at the edge of a substrate plate segment from the applied material during the production operation. That procedure has the advantage that it is possible to dispense with structurally complicated and expensive separating wall tracking guidance systems. Instead, along the edge region of a substrate plate segment, a suitable separating wall is built up, which can then also be removed upon removal of the products from the substrate plate segment or is removed in the course of the removal of unhardened material from the adjacent substrate plate segment.

In that respect it is particularly preferred if the separating wall between two substrate plate segments is joined to at least one of the two substrate plate segments. Joining the separating wall to both substrate plate segments, which separates them from each other, at the same time also provides for secure sealing integrity to prevent material from passing through between the substrate plate segments. In that case the connection of the separating wall can be achieved by generative construction of the separating wall on one or both substrate plate segments or by suitably constructive connection of a separating wall component which belongs to the apparatus.

In accordance with still a further preferred embodiment it is provided that in a first production portion the material is applied to the substrate plate in a quasi-continuous process and predetermined regions of a respectively applied layer are selectively hardened and in a second production portion products in the finished hardened state are quasi-continuously removed. That configuration provides a quasi-continuous, generative production procedure which is distinguished by high productivity and which at the same time can also generatively produce very small products in a very short period of time. That mode of operation permits high-quality generative production in a first production portion and at the same time removal of finished products in a second production portion which is spaced from the first production portion, without negatively affecting such generative production. That can be achieved in particular by means of an endless conveyor belt on which the substrate plate segments are arranged or which is formed by the substrate plate segments. In particular with this configuration the first production portion can be kept in a closed-off inert atmosphere in order to be able to set the boundary condition required for generative production in accordance with given processes, whereas the second production portion permits discharge of the products or the products are already discharged from the inert atmosphere at the transition from the first to the second production portion.

It is still further preferred if the hardened regions of the previously applied layer are subjected to surface grinding prior to each material application operation. Such a surface treatment which in particular can be effected in the form of a grinding operation but can also be implemented by other cutting production processes with a geometrically defined or geometrically undefined cutting edge means that the geometrical precision of the generative production process is still further enhanced. In particular such a cutting treatment provides a defined contact surface and connecting location for the layer disposed thereabove and the regions to be hardened therein. In addition the cutting treatment sets a defined layer thickness, and that is advantageous for a reproducible geometrical production result.

It is still further preferred if a single radiation source, in particular a single beam path of a single radiation source, is used for hardening the product or products on the substrate plate, in particular on all substrate plate segments. Basically it is to be appreciated that, to accelerate the production operation, it is also possible to have recourse to a plurality of beam sources or a plurality of beam paths of a single beam source. The production process according to the invention however is distinguished in particular in that admittedly a plurality of products are produced at the same time and those products are at different production stages, that is to say are made up in particular from a different number of layers. What is particular in that respect however is that both the application of a layer can be effected by a single layer application apparatus for all substrate plate segments and products which are built up thereon and which are to be finished, and in addition hardening of the given regions of a layer can be effected for all products to be finished, by a single radiation source.

Finally a further development of the process according to the invention can involve the steps of: applying an n-th material layer to a substrate carrier plate, selectively hardening parts of the material layer by means of the action of an energy-rich radiation, in particular a laser radiation, on those parts of the material layer, guiding the energy-rich radiation over the n-th material layer in accordance with guidance data which were ascertained from the geometrical data of an x-th cross-sectional area of a first product, applying an n+1-th material layer to the n-th material layer, guiding the energy-rich radiation over the n+1-th material layer in accordance with guidance data which were ascertained from the geometrical data of an x+1-th cross-sectional area of the first product, guiding the energy-rich radiation over the n-th material layer in accordance with guidance data which were ascertained from the geometrical data of a y-th cross-sectional area of a second product, and guiding the energy-rich radiation over the n+1-th material layer in accordance with guidance data which were ascertained from the geometrical data of a y+1-th cross-sectional area of the second product, wherein x is unequal to y.

In that development at least two products are produced by one and the same layer being subjected to selective hardening in a common layer application in two different layer regions, wherein different heights in relation to the substrate plate are represented in that layer in the products themselves.

A further aspect of the invention is an apparatus for producing products of individual geometry, including a substrate plate, a material application apparatus for applying material layers to and above the substrate plate, a radiation source for a high-energy beam, beam guidance means for guiding the beam on to predetermined regions of a material layer applied to the substrate plate, in which according to the invention the material application apparatus is adapted to apply the material in a plane which is oriented inclinedly, in particular at an angle which is less than or equal to the angle of repose of the material, relative to the surfaces of the substrate plate, to which the material is applied.

The apparatus according to the invention proposes a generative production apparatus which can generatively produce small products quickly with a high level of productivity. The apparatus according to the invention is distinguished in that the material application apparatus with which the material layers are applied to the substrate plate is of such a design configuration that said layer application can be implemented inclinedly relative to the surface of the substrate plate.

A development of the apparatus according to the invention can provide that the substrate plate is subdivided into a plurality of substrate plate segments and the material application apparatus is adapted for simultaneous application of a material layer to a number of the plurality of substrate plate segments.

The apparatus according to the invention can be still further developed in that the substrate plate segments are connected releasably together or releasably to a main carrier.

A further preferred embodiment provides that the substrate plate segments and the material application apparatus are movable relative to each other in such a way that the maximum spacing between a first substrate plate segment and a material layer applied above that substrate plate segment for production of the first product differs from the maximum spacing between a further substrate plate segment and a material layer applied above that further substrate plate segment for producing a further product.

A further preferred configuration is distinguished by a material removal apparatus, in particular a material suction removal device, wherein the material removal apparatus is adapted to remove unhardened material from a region surrounding a finished product, and is so arranged that it removes the material around a finished product on a first substrate plate segment and in so doing leaves the material around a product on a further substrate plate segment adjacent thereto.

It is still further preferred if the apparatus according to the invention has a control for actuation of the guidance device of the high-energy beam, which is adapted to actuate the guidance device in such a way that in a first phase of the production operation only layer regions of a layer which serve for producing a first product on a first substrate plate segment are selectively hardened, in a last phase of the production operation only layer regions of a layer which serve to produce a further product on a further substrate plate segment are selectively hardened and in a middle phase in the production operation, that is between the first and last phases, layer regions of a layer are selectively hardened, which serve to produce the first and the further product.

It is further preferably provided that the substrate plate segments are arranged on an endless conveyor belt which extends partially or completely in a processing chamber which is sealed off in relation to the environment to such an extent that a controlled, in particular inert atmosphere can be set therein and preferably the material application apparatus is so designed that the material is applied in the first direction, preferably at such an angle to the surface of the respective substrate plate segment that the direction of flow of the material is in opposite relationship to the application direction.

In a further preferred embodiment the apparatus according to the invention has a separating wall which is arranged between the substrate plate segments and which separates the building space above each substrate plate segment from the building space above an adjacent substrate plate segment.

In that respect it is particularly preferred if the separating wall between two substrate plate segments is connected to at least one of the two substrate plate segments or is sealed off in relation to said substrate plate segment in such a way that no material can pass through between the separating wall and the substrate plate segment.

It is still further preferred if there is provided a control for actuation of the guidance device of the high-energy beam, which is adapted to actuate the guidance device in such a way that the separating wall is produced during the product production operation by hardening of the applied material.

Particularly preferably the apparatus according to the invention has a single radiation source which is used in particular by means of a single beam path for hardening of all products, in particular the products produced on all substrate plate segments.

It is still further preferred if there is provided a control for actuation of the guidance device of the high-energy beam, which is adapted to guide the energy-rich radiation over the n-th material layer in accordance with guidance data which were ascertained from the geometrical data of an x-th cross-sectional area of a first product, to harden parts of the n-th material layer by means of the action of an energy-rich radiation, to guide the energy-rich radiation over an n+1-th material layer in accordance with guidance data which were ascertained from the geometrical data of an x+1-th cross-sectional area of the first product to harden parts of the n+1-th material layer by means of the action of the energy-rich radiation, to guide the energy-rich radiation over the n-th material layer in accordance with guidance data which were ascertained from the geometrical data of a y-th cross-sectional area of a second product to harden parts of the n-th material layer by means of the action of the energy-rich radiation and to guide the energy-rich radiation over the n+1-th material layer in accordance with guidance data which were ascertained from the geometrical data of a y+1-th cross-sectional area of the second product to harden parts of the n+1-th material layer by means of the action of the energy-rich radiation, wherein x is unequal to y.

Finally a development of the apparatus according to the invention can provide that arranged at the material application apparatus is a treatment apparatus for removing a part of the hardened material regions, preferably for surface grinding of the hardened material regions of a previously applied material layer.

Figure 2:
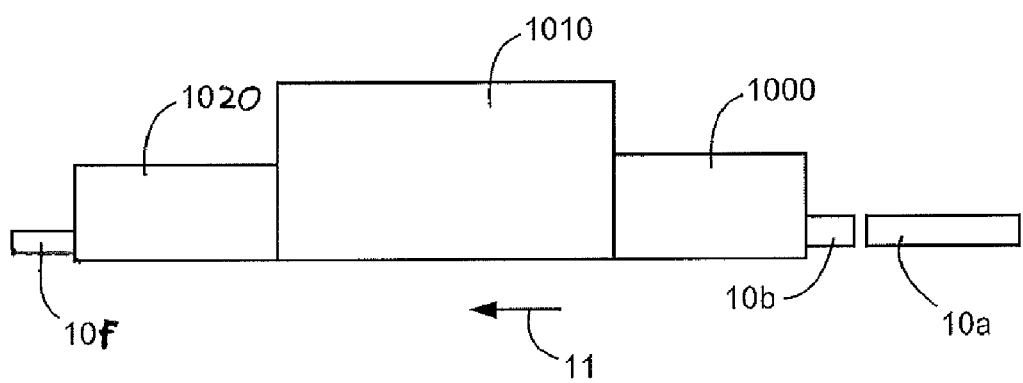
Figure 3:
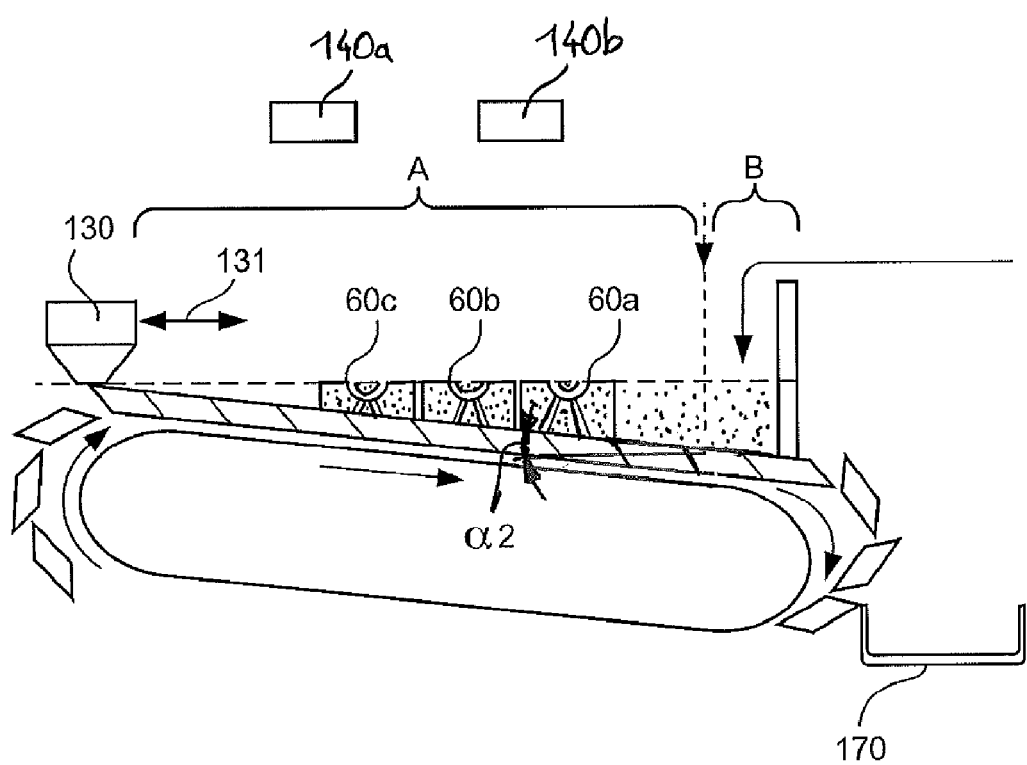
Figure 4:
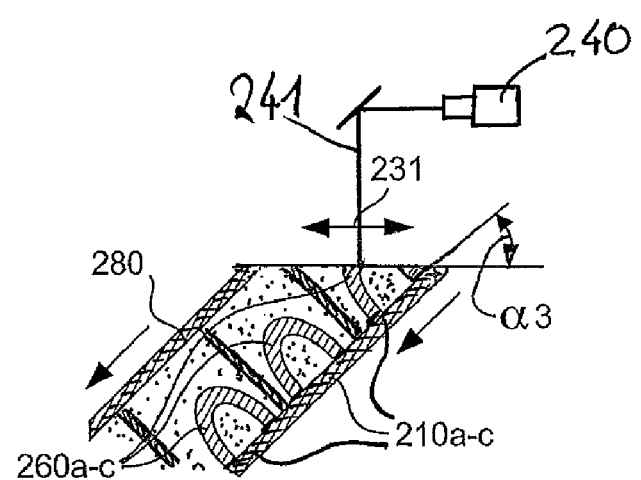
Figure 5:
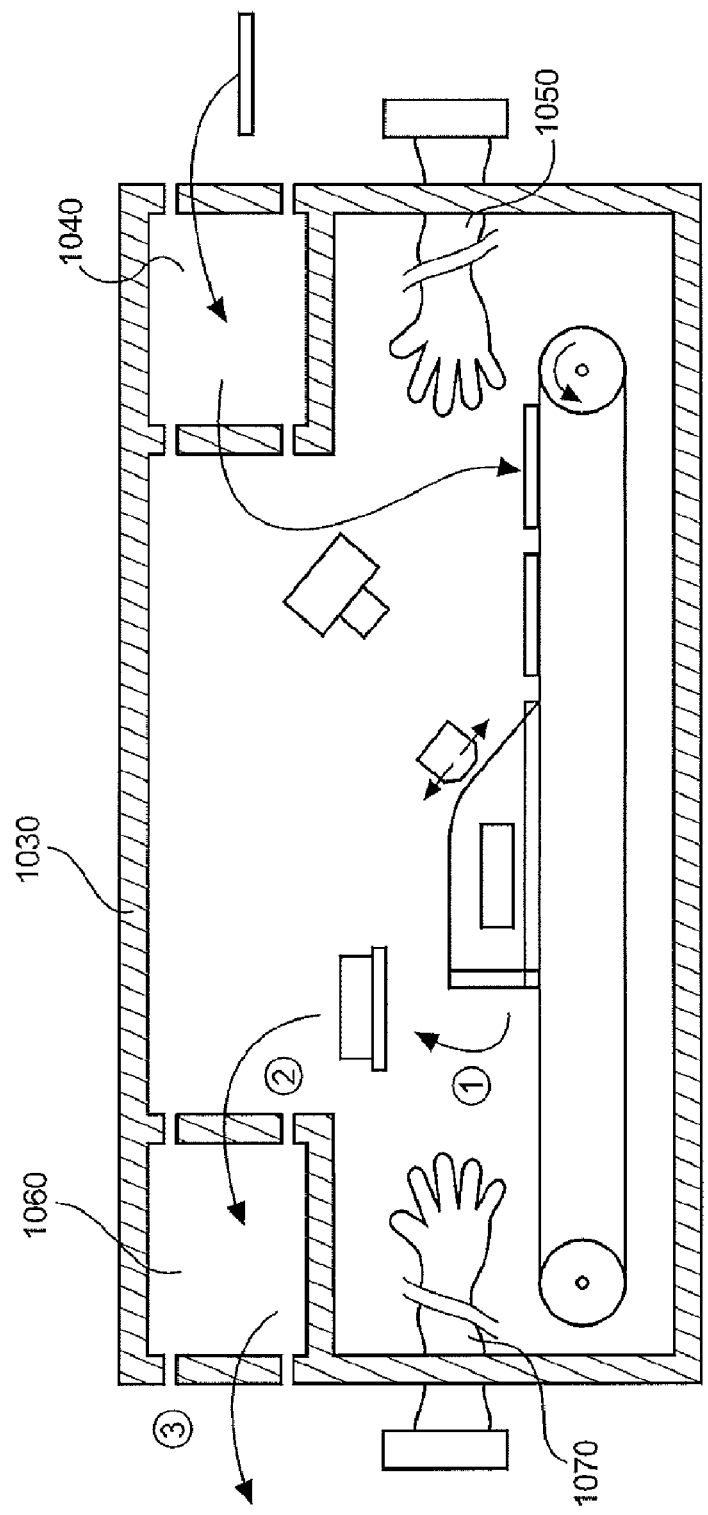

Preferred embodiments of the invention are described with reference to the accompanying Figures in which:

FIG. 1 shows a diagrammatic side view in longitudinal section of a production portion of a generative production section according to the invention, FIG. 2 shows a diagrammatic view illustrating the principle of a production arrangement according to the invention, FIG. 3 shows a diagrammatic side view in longitudinal section of a production portion with an endless conveyor belt, FIG. 4 shows a diagrammatic side view in longitudinal section of a production portion of a further embodiment of the invention, and FIG. 5 shows a diagrammatic view of a production arrangement according to the invention.

FIG. 1 shows a substrate plate 10 comprising a plurality of substrate plate segments 10a-c. The substrate plate segments 10a-c are releasably connected to the substrate plate carrier 20 arranged therebeneath. The substrate plate carrier 20 and the substrate plate segments 10a-c are arranged in such a way that the surface of the substrate plate segments 10a-c is oriented horizontally, that is to say perpendicularly to the direction of the force of gravity, in the operating condition of the apparatus.

A coating apparatus 30 is arranged above the upper contact surface of the substrate plate segments 10a-c in the direction of the force of gravity. The coating apparatus 30 is displaceable in a direction of movement 31. The direction of movement 31 is in a straight line and includes an angle α with the plane defined by the upper contact surface of the substrate plate segments 10a-c. A powder layer which is inclined at an angle α relative to the horizontal can be applied by cyclic reciprocating movement of the coating apparatus 30 along the direction of movement 31, above the substrate plate segments 10a-c.

A heating means can be incorporated in each substrate plate segment 10a-c which keeps the substrate plate segment and the powder bed disposed thereon at a desired temperature. By virtue thereof and by virtue of one or more optionally additionally provided radiating device arrays and/or heating belts in the region of the coating apparatus, which heat the applied powder layer or maintain the temperature thereof, the apparatus can be optimised in such a way as to achieve a desired, preheated condition for the powder prior to the selective hardening operation.

The substrate plate segments 10a-c can be advanced continuously or in a cyclically controlled, quasi-continuous fashion in a direction of movement 11 which is parallel to the horizontal. By means of the direction of movement 11, after application of a layer by means of the coating apparatus 30, a spacing which corresponds to the layer height of the next layer to be applied is produced between the plane in which the coating apparatus 30 moves and the applied layer.

A radiation source 40 which is a high-power laser is arranged in such a way that its beam is incident on the surface of an applied layer approximately perpendicularly and preferably precisely perpendicularly. The beam of the radiation source 40 can be deflected with beam deflection means in such a way that it is incident on predetermined regions of an applied layer and selectively hardens same.

The beam deflection means are coupled to a control apparatus by signal technology. Production data for at least the products which are to be respectively produced simultaneously are stored in the control apparatus. The production data include in particular positional data which characterise the position of a respective product on the substrate plate and geometry data characterising the geometry of the respective product. The geometry data are processed in such a way that the geometrical data of individual cross-sections of the product are contained therein. The respective position of such a cross-section and the geometry data stored for that cross-section corresponds to the position of the respectively applied material layer from which that product cross-section is produced and the geometry of the product in that material layer. In the illustrated embodiment with products standing up perpendicularly on the plate, the geometrical data therefore correspond to inclinedly extending cross-sectional planes through that product.

As will be seen, a powder bed is applied above the substrate plate segment 10c, the powder bed being composed of a plurality of powder layers and being of the maximum height h above the substrate plate segments. That maximum height is also already attained above the substrate plate segment 10b in a region that is to the left, but it will be noted that it is not yet completely attained in a region which is to the right thereof and which is in opposite relationship to the conveyor direction 11. Instead, in that right-hand region of the substrate plate segment 10b the surface of the powder bed extends inclinedly at the angle α1, just as in a left-hand region of the substrate plate segment 10c.

A generatively produced product 60b is arranged in the powder bed in hardened form above the substrate plate segment 10b. In the same manner a product 60c is generatively produced above the substrate plate segment 10a. That production operation is effected by a procedure whereby, after the application of each powder layer 51, predetermined regions of that powder layer are selectively hardened by means of the radiation source 40. Thereupon, by an advance movement of the substrate plate segments in the conveyor direction 11, a spacing corresponding to the layer height is produced between the plane of the coating apparatus 30 and the previously applied layer and thereafter a renewed coating operation is effected by movement of the coating apparatus 30 along the direction of movement 31. A grinding device can preferably be arranged at the coating apparatus. The grinding device can either be arranged in the direction of movement in the powder application operation upstream of the position at which the powder is applied, and serves and is adapted to implement initial surface grinding of the previously hardened regions. In that way the geometrical truth of the generatively produced product can be improved and binding of the subsequent regions to be hardened thereto can be increased. As an alternative thereto it is possible to carry out the grinding operation in a return stroke movement of the coating apparatus, that is to say between the production step of selective hardening and the production step of renewed powder application. In that case the arrangement of the grinding device on the coating apparatus in relation to the position at which the powder is applied can be structurally freely selected as the grinding operation and the powder application operation are not effected during one and the same movement of the coating apparatus.

That procedure is repeatedly performed until the entire product 60c is produced. The conveyor movement 11 provides that the products 60b, c which are generatively produced and finished in that way are further conveyed towards the left where, after suitable removal of the unhardened powder from the substrate plate, they can be removed.

In that respect FIG. 2 shows a possible construction of a production arrangement and a corresponding operating procedure. As will be seen the substrate plate segments 10a, b, c . . . are charged into an intake charging lock 100 from a right-hand side in a horizontal direction of movement 11 and pass in the same direction of movement 11 out of the intake charging lock 100 into a process chamber 110. The production portion shown in FIG. 1 is disposed in the process chamber 110 and the production operation described with reference to FIG. 1 takes place. After suitable generative production of the products in the process chamber 110 they pass into an outlet discharging lock 120 by further movement in the direction of movement 11 and are thereby discharged from the process chamber.

Intake charging of the uncoated substrate plate segments through the intake charging lock 100 and discharge of the coated substrate plate segments bearing generatively produced products through the outlet discharging lock 120 means that it is possible to maintain in the process chamber 110 an atmosphere which is favourable to generative production, in particular an inert gas atmosphere or an active gas atmosphere, thereby ensuring product quality.

FIG. 3 shows a second embodiment of a production portion for generative production and a production portion for separation and removal of generatively produced products. A plurality of substrate plate segments 110a, b, c . . . is arranged in mutually juxtaposed relationship in such a way that a cohesive substrate plate is afforded thereby. The upper surface of that substrate plate provided by the substrate plate segments 110a, b, c is inclined at an angle $\alpha$ relative to the horizontal, that is to say that surface is at an angle 90°—$\alpha$ relative to the direction of the force of gravity.

Arranged above the substrate plate segments 110a, b, c . . . is a coating apparatus 130 which can cyclically reciprocate along a horizontal direction of movement 131. In that way, the coating apparatus 130 can be used to apply a powder layer from a powder reservoir which can be arranged at the coating apparatus 130 or which can be arranged along the path of movement 131 of the coating apparatus 130.

A powder layer can be applied by means of the coating apparatus 130 by movement along the coating direction 131, above the substrate plate segments 110a, b, c . . . , the powder layer being at an angle $\alpha$ relative to the upper surface of the substrate plate segments.

Predetermined regions of each powder layer are selectively hardened on the substrate plate segments 110a, b, c . . . by selective hardening of each applied layer by means of two radiation sources 140a, b in the form of high-power lasers, and thereby products 60a, b are layer-wise generatively built up on the substrate plate segments. In addition, separating walls 61a-d are respectively built up above the substrate plate segments by suitably selective hardening of the layers between each product or between a group of products. Those separating walls subdivide the powder bed above the substrate plate segments into a plurality of powder bed regions. A product or a plurality of products are arranged in each powder bed region, which can be simultaneously removed.

The substrate plate segments 110a, b, c . . . are fixed to an endless conveyor belt 120 and are continuously or discontinuously advanced in a conveyor direction 111 by means of the endless conveyor belt 120. In a production portion A, generative production of the products is effected by that conveyor movement 111 and repeated application of powder layers by means of the coating apparatus 130, followed by selective hardening of each applied layer. The powder coating apparatus 130 moves in that case in a direction of movement 131 which is at an angle $\alpha 2$ relative to the direction of movement 111 of the substrate plate segments.

In a production region B unhardened powder material is removed by a suction removal apparatus from the region between two generatively produced separating walls 61a-d and thereupon both the separating walls and also the products generatively produced and finished in that region between the two separating walls are removed. Downstream of the production portion B in the conveyor direction 110, the substrate plate segments are guided along a direction-changing roller into the lower run of the conveyor belt 120 and pass along that lower run to a second direction-changing roller at which they are again guided into the upper run in order to be passed to a renewed coating operation using powder layers and generative production of products.

A catch trough 170 is provided to catch excess powder which drops off upon the change in direction of the substrate plate segments.

As can be seen from FIG. 3 individual products can be generatively constructed on a single substrate plate segment or a single product can also be generatively constructed on a plurality of substrate plate segments. In that respect, whether a plurality of products are produced on a substrate plate segment or one product is produced on a plurality of substrate plate segments or a respective product is produced for each substrate plate segment depends solely on the size of the substrate plate segments and the products generatively produced thereon. In particular, by the use of supports, it is also possible to produce a product on a single substrate plate segment, the dimensions of which are larger than the dimensions of the substrate plate segment itself.

Both in the FIG. 1 embodiment and also in the FIG. 3 embodiment, the angle $\alpha 1$ or $\alpha 2$ respectively between the layer application direction and the surface of the substrate plate segments is smaller than the angle of repose of the applied powder in order thereby to achieve stability for the applied powder bed in relation to the action of the force of gravity. In principle, in the FIG. 3 embodiment, the angle $\alpha 2$ could also be larger than that angle of repose of the powder as the powder bed is stabilised by the separating walls 61a-d and the powder layers themselves are horizontally applied and are disposed horizontally.

FIG. 4 shows a diagrammatic view of an alternative embodiment in which the angle $\alpha 3$ between the plane in which the powder layer application is effected and the surface of the substrate plate segments can be larger than the angle of repose of the powder. In this embodiment the products 260a-c are also generatively built up on substrate plate segments 210a-c and in that case a powder bed 250 is produced above those substrate plate segments. The powder bed 250 is stabilised by means of a cover plate 280 extending parallel to the substrate plate segments in the production portion. In this case the cover plate 280 can in particular continuously advance with the substrate plate segments to prevent a relative movement between the powder bed and the cover plate 280.

FIG. 5 shows a diagrammatic view of a production arrangement for the continuous production of generatively produced products. The FIG. 5 embodiment represents an alternative to the embodiment shown in FIG. 2. Contrary to the FIG. 2 embodiment, the FIG. 5 embodiment provides that all production portions required for generative production and removal of the products from the generative production process are arranged within a process chamber 1030 which is kept under a controlled atmosphere, in particular an inert gas or active gas atmosphere.

As can be seen, arranged within the process chamber 1030 is a production process whose system in principle corresponds to the production process of FIG. 1. It will be appreciated however that in the same way the production arrangement shown in FIG. 5 can also be of such a configuration that a production process as shown in FIG. 3 or FIG. 4 takes place in the process chamber. The process chamber 1030 has a first intake charging lock 1040 through which fresh uncoated substrate plates not bearing products can be introduced and can be fixed on an endless conveyor belt. To be able to perform that operation manually, a working glove 1050 is gas-tightly arranged in such a region which permits substrate plates to be received from the charging lock 1040 and fixed on the endless conveyor belt.

In addition a second lock 1060 is arranged on the process chamber 1030. Substrate plates with finished products arranged thereon can be discharged from the process chamber 1030 through the discharge lock 1060. To be able to perform that operation manually once again arranged in the region of the lock 1060 is a glove, by means of which it is possible to engage into the process chamber 130, the substrate plate segments together with products arranged thereon can be removed from the endless conveyor belt and can be discharged from the process chamber 1030 through the lock 1060.

What is claimed is:

1. A process for producing products of individual geometry, comprising the steps:
    applying a hardenable material in successive layers;
    selectively hardening one or more predetermined regions after each layer application by means of an energy-rich radiation and in so doing connecting said regions to one or more regions of the subjacent layer;
    wherein the predetermined region or regions is or are predetermined on the basis of a cross-sectional geometry of the product in the respective layer;
    characterized in that the successive layers are applied in layer planes which are oriented inclinedly relative to the surface of the substrate plate;
    further characterized in that the substrate plate is displaced between two successive layer application operations with a directional component perpendicularly to the plane in which the layer is applied.

2. The process according to claim 1 characterized in that each of the successive layers is applied at an angle which is less than or equal to the angle of repose of the material.

3. The process according to claim 1 characterized in that the surface of the substrate plate is subdivided into a first surface of a first substrate plate segment and at least one further surface of a further substrate plate segment.

4. The process according to claim 3 characterized in that the substrate plate segments are connected releasably to each other or releasably to a main carrier and each substrate plate segment after production of one or more products on the surface thereof is released from an adjacent substrate plate segment or the main carrier in order to feed the product or products thereon to further processing steps.

5. The process according to claim 3 characterized in that in the production portion in which the layers are applied the substrate plate segments are so provided in mutually juxtaposed relationship that no material can pass through between the substrate plate segments.

6. The process according to claim 3 characterized in that the substrate plate segments are in the form of segments of an endless conveyor apparatus.

7. The process according to claim 3 characterized in that provided between the substrate plate segments is a separating wall which separates the building space above each substrate plate segment from the building space above an adjacent substrate plate segment.

8. A process for producing products of individual geometry, comprising the steps:
    applying a hardenable material in successive layers;
    selectively hardening one or more predetermined regions after each layer application by means of an energy-rich radiation and in so doing connecting said regions to one or more regions of the subjacent layer;
    wherein the predetermined region or regions is or are predetermined on the basis of a cross-sectional geometry of the product in the respective layer;
    characterized in that the successive layers are applied in layer planes which are oriented inclinedly relative to the surface of the substrate plate;
    further characterized in that the surface of the substrate plate in the region in which the layers are applied extends inclinedly relative to the horizontal in relation to the direction of the force of gravity.

9. A process for producing products of individual geometry, comprising the steps:
    applying a hardenable material in successive layers;
    selectively hardening one or more predetermined regions after each layer application by means of an energy-rich radiation and in so doing connecting said regions to one or more regions of the subjacent layer;
    wherein the predetermined region or regions is or are predetermined on the basis of a cross-sectional geometry of the product in the respective layer;
    characterized in that the successive layers are applied in layer planes which are oriented inclinedly relative to the surface of the substrate plate;
    further characterized in that the applied layers are displaced into an adjacent production portion which is disposed adjacent to a production portion in which the layers are applied and which is in the form of a holding region and in which an upper surface, formed by the applied layers, of the applied material is covered and supported by a lower surface of a cover plate, the lower surface extending parallel to the surface of the substrate plate.

10. A process for producing products of individual geometry, comprising the steps:
    applying a hardenable material in successive layers;
    selectively hardening one or more predetermined regions after each layer application by means of an energy-rich radiation and in so doing connecting said regions to one or more regions of the subjacent layer;
    wherein the predetermined region or regions is or are predetermined on the basis of a cross-sectional geometry of the product in the respective layer;
    characterized in that the successive layers are applied in layer planes which are oriented inclinedly relative to the surface of the substrate plate;

further characterized in that the surface of the substrate plate is subdivided into a first surface of a first substrate plate segment and at least one further surface of a further substrate plate segment;

further characterized in that provided between the substrate plate segments is a separating wall which separates the building space above each substrate plate segment from the building space above an adjacent substrate plate segment; and further characterized in that the separating wall is produced by hardening of the applied material during the production operation of the product or products.

* * * * *